United States Patent [19]

Gunther et al.

[11] Patent Number: 5,208,336

[45] Date of Patent: May 4, 1993

[54] SELENOMEROCYANINES AND PROCESSES FOR PREPARATION AND METHODS OF USE AND COMPOSITIONS THEREOF

[75] Inventors: Wolfgang H. H. Gunther, Chester County, Pa.; Roger Searle, Sand Lake, N.Y.

[73] Assignee: Sterling Drug Inc., New York, N.Y.

[21] Appl. No.: 599,961

[22] Filed: Oct. 19, 1990

[51] Int. Cl.$^5$ ............... C07D 413/06; C07D 417/06; C07D 421/06; G03G 5/06

[52] U.S. Cl. ................................. 544/300; 430/590

[58] Field of Search ........................... 544/300

[56] References Cited

U.S. PATENT DOCUMENTS

| | | | |
|---|---|---|---|
| 4,775,625 | 10/1988 | Sieber | 544/300 |
| 4,885,366 | 12/1989 | Gunther et al. | 544/300 |
| 4,906,750 | 3/1990 | Gunther et al. | 544/300 |
| 4,937,344 | 6/1990 | Gunther et al. | 544/300 |
| 5,053,506 | 10/1991 | Gunther et al. | 544/300 |

*Primary Examiner*—Cecilia Tsang
*Attorney, Agent, or Firm*—Theodore C. Miller; Paul E. Dupont; Imre Balogh

[57] ABSTRACT

Selenomerocyanines, for example the compound having the structural formula

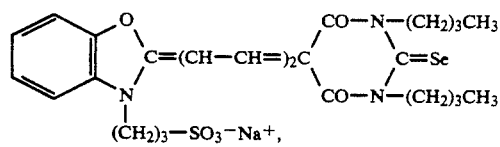

a process for preparation thereof, methods of use thereof as photosensitizers for generation of singlet oxygen, virus inactivation and cancer cell inactivation, and photosensitized silver halide photographic emulsions containing them are disclosed.

17 Claims, No Drawings

SELENOMEROCYANINES AND PROCESSES FOR PREPARATION AND METHODS OF USE AND COMPOSITIONS THEREOF

BACKGROUND OF THE INVENTION

1. Field of the Invention

The invention relates to selenomerocyanines, a process for preparation thereof, methods of use thereof as photosensitizers for generation of singlet oxygen, virus inactivation and cancer cell inactivation, and photosensitized silver halide photographic emulsions containing them.

2. Information Disclosure Statement

Sieber U. S. Pat. No. 4,775,625 issued Oct. 4, 1988 describes methods of inactivating enveloped viruses and treating diseases thereof by photoactivation of merocyanine dyes, especially Merocyanine 540 (MC 540) having the structural formula:

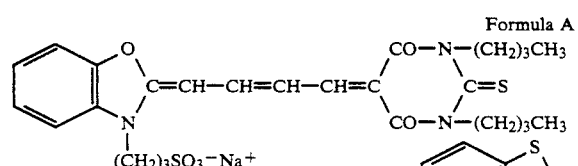

Formula A

Gunther et al. U.S. Pat. No. 4,885,366 issued Dec. 5, 1989 describes selenazole merocyanine dyes useful for inactivating viruses and leukemia cells by photoactivation, for example the compound having the structural formula:

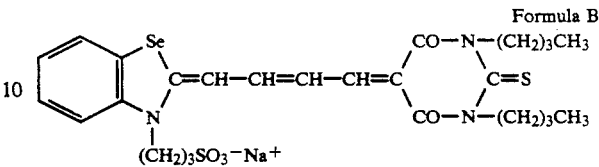

Formula B

Gunther et al. U.S. Pat. No. 4,906,750 issued Mar. 6, 1990 describes oxazole merocyanine dyes useful for inactivating viruses and leukemia cells by photoactivation, for example the compound having the structural formula:

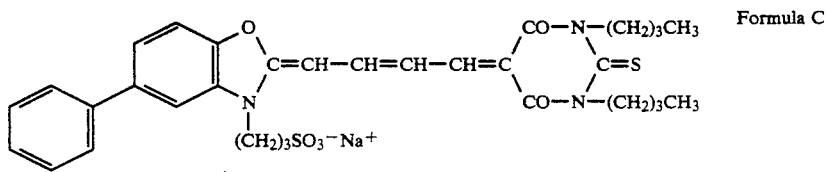

Formula C

Gunther et al. U.S. Pat. No. 4,937,344 issued Jun. 26, 1990 describes thiazole merocyanine dyes useful for inactivating viruses and leukemia cells by photoactivation, for example the compounds having the structural formulas:

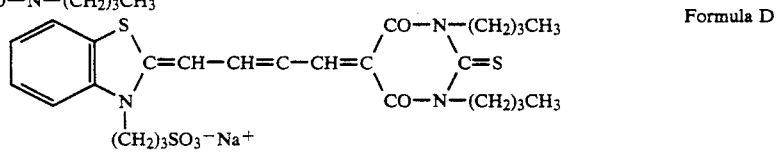

Formula D

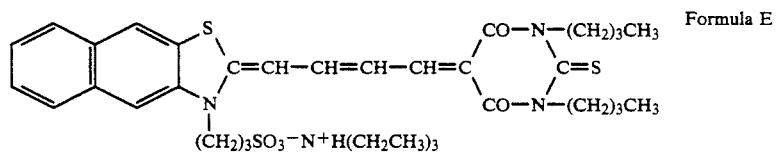

Formula E

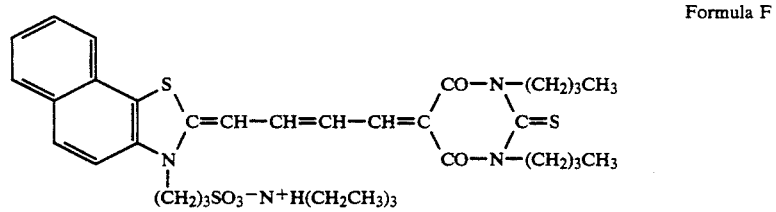

Formula F

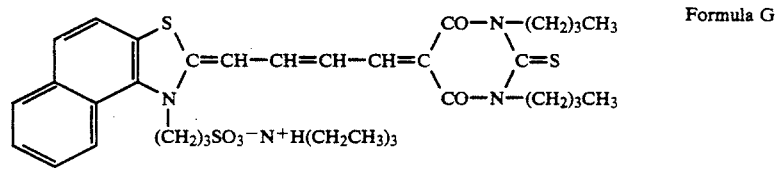

Formula G

SUMMARY OF THE INVENTION

In a first composition of matter aspect the invention is a compound having the structural formula

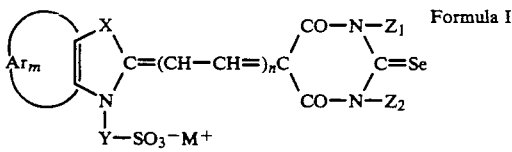

Formula I wherein
- X is O, S, Se, Te, C(CH$_3$)$_2$ or NR wherein R is methyl, ethyl, propyl, cyclopropyl, cyclohexyl, phenyl or phenyl substituted by from one to three of methyl, trifluoromethyl, methoxycarbonyl, ethoxycarbonyl, cyano, dimethylamino, methoxy, methylthio, fluoro, chloro, bromo, or iodo;
- Y is alkylene having from two to nine carbon atoms or alkylene having from two to nine carbon atoms interrupted by O, S, NR', CONH or phenylene wherein R' is methyl, ethyl or phenyl;
- Z$_1$ and Z$_2$ are independently H or alkyl having from one to ten carbon atoms;
- m is 0 or 1;
- n is 1, 2 or 3;
- M$^+$ is a pharmaceutically or photographically acceptable cation; and Ar is a fused aromatic nucleus having from one to three carbocyclic or carbon-nitrogen heterocyclic rings.

The compounds of Formula I are useful as photosensitizers for generation of singlet oxygen, inactivation of viruses, inactivation of cancer cells and sensitization of silver halide photographic emulsions.

In a first process aspect the invention is the process for preparing a compound of Formula I comprising condensing the corresponding compound having the structural formula

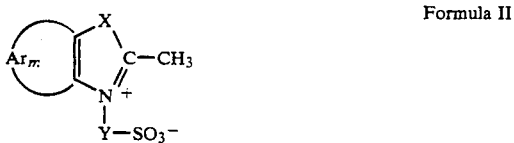

Formula II with the corresponding compound having the structural formula

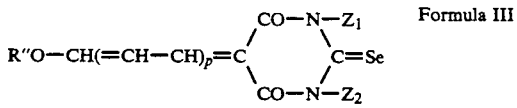

Formula III wherein R" is methyl or ethyl and p is 0, 1 or 2 using a basic tertiary amine catalyst in an inert solvent at a temperature in the range from 0° C. to 100° C.

In a second process aspect the invention is the method of generating singlet oxygen comprising illuminating a solution of a compound of Formula I in an inert solvent with visible light in the presence of oxygen.

In a third process aspect the invention is the method of inactivating a susceptible virus comprising contacting the virus with an inactivatingly effective amount of a compound of Formula I and illuminating the resulting mixture with visible light.

In a fourth process aspect the invention is the method of inactivating susceptible cancer cells comprising contacting the cancer cells with an inactivatingly effective amount of a compound of Formula I and illuminating the resulting mixture with visible light.

In a second composition of matter aspect the invention is a photosensitized silver halide photographic emulsion containing a photosensitizingly effective amount of a compound of Formula I.

DETAILED DESCRIPTION OF THE INVENTION INCLUSIVE OF THE PREFERRED EMBODIMENTS

Definitions

In Y of the compounds of Formula I alkylene having from two to nine carbon atoms can be branched or unbranched and is preferably (CH$_2$)$_q$ wherein q is 2, 3 or 4 and most preferably (CH$_2$)$_3$.

In Z$_1$ and Z$_2$ of the compounds of Formula I alkyl having from one to ten carbon atoms can be branched or unbranched and is preferably (CH$_2$)$_r$CH$_3$ wherein r is an integer from 2 to 9 and most preferably (CH$_2$)$_3$CH$_3$.

In the compounds of Formula I the pharmaceutically or photographically acceptable cation (M$^+$) is any natural or synthetic pharmaceutically or photographically acceptable cation, preferably an alkali or alkaline earth metal cation or an ammonium ion derived from ammonia or a pharmaceutically or photographically acceptable amine, most preferably sodium ion or triethylammonium ion. Pharmaceutical utility of a compound of Formula I requires a pharmaceutically acceptable cation. Photographic utility of a compound of Formula I requires a photographically acceptable cation.

In the compounds of Formula I wherein m is 1 the fused aromatic nucleus having from one to three carbocyclic or carbon-nitrogen heterocyclic rings generally has from one to three six-membered rings but can have a five-membered or seven-membered ring instead. One or two six-membered rings including benzo, naphtho, pyrido, pyrazino, pyridazino, pyrimidino, quinolino, isoquinolino, quinoxalino, cinnolino, phthalazino, quinazolino and quinolizino are preferred. Benzo and naphtho are most preferred.

In the process for preparing the compounds of Formula I "corresponding" means that the variables of the compound of Formula II and the compound of Formula III used to prepare a particular compound of Formula I are the same as those of the compound of Formula I. The same meaning applies to the preparation of the compounds of Formula II and the compounds of Formula III and the precursors thereof described below. The basic tertiary amine catalyst can be any basic aliphatic, aromatic or aliphatic-aromatic amine, preferably a trialkylamine, most preferably triethylamine. An "inert solvent" is one which dissolves the reactants and catalyst but does not react adversely with them or with the product and can be any such solvent or mixture thereof. The same meaning applies to the preparation of the compounds of Formula II and the compounds of Formula III and the precursors thereof described below. A nonaqueous solvent is preferred. Acetonitrile is most preferred.

If a molar equivalent quantity or more of basic tertiary amine catalyst is used, M$^+$ of the resulting compound of Formula I is the corresponding basic tertiary ammonium ion, for example, triethylammonium ion, which can itself be a pharmaceutically or photographically acceptable cation or can be exchanged by ion exchange to produce the desired pharmaceutically or photographically acceptable cation.

In the biological methods of use inactivating means killing, destroying, reducing the number of, reducing the replication of, and/or reducing an adverse effect of the virus or cancer cells. Susceptible means capable of being inactivated by the method. The susceptible viruses and cancer cells are readily identified and the inactivatingly effective amounts of the compounds of Formula I are readily determined by tests such as those described below.

Preparation of the Compounds

The compound of Formula II is prepared by condensing the corresponding compound having the structural formula

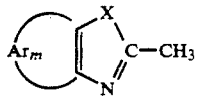   Formula IV with the corresponding compound having the structural formula

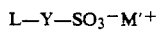   Formula V wherein l is a leaving group and $M'^+$ is $H^+$ or $M^+$ or L and $M'^+$ taken together are a bond with or without an inert solvent at a temperature in the range from 0° to 100° C. The leaving group L can be any atom or group of atoms anionic in character and displaceable by the compound of Formula IV at the nitrogen atom, for example, chloro, bromo or iodo. When Y is $(CH_2)_3$, L and $M'^+$ are preferably a bond, that is, the compound of Formula V is 1,3-propanesultone and the preferred inert solvent is acetonitrile. The compounds of Formula IV and the compounds of Formula V are generally known and, if not specifically known, preparable by known methods. The compounds of Formula II wherein X is O or S, m is 1, Ar is benzo and Y is $(CH_2)_3$ and the compounds of Formula II wherein X is S, m is 1, Ar is naphtho[1,2-d], naphtho[2,1-d] or naphtho[2,3-d] and Y is $(CH_2)_3$, which are the preferred compounds of Formula II, are prepared by condensing the corresponding compounds of Formula IV with 1,3-propanesultone in the melt or in acetonitrile or butyronitrile.

The compound of Formula III is prepared by condensing the corresponding compound having the structural formula

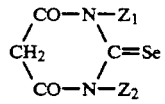   Formula VI with the corresponding compound having the structural formula

   Formula VII wherein R" is methyl or ethyl in an inert solvent at a temperature in the range from 0° to 100° C. The preferred inert solvent is acetone. The compounds of Formula VII are generally known and, if not specifically known, preparable by known methods. In an example the mother liquor from the below-described hexane crystallization of 1,3-dibutyl-2-selenobarbituric acid (the compound of Formula VI wherein $Z_1$ and $Z_2$ are each $(CH_2)_3CH_3$, theoretically 26.8 g.) was added to a solution of 1,1,3-trimethoxypropene (the compound of Formula VII wherein R' is methyl and p is 1, 20 g.) in acetone (100 ml.) with stirring at room temperature. The mixture quickly set to an orange solid, which was collected after 30 minutes, washed with acetone to remove a red contaminant and air dried affording the compound of Formula III wherein R' is methyl, p is 1 and $Z_1$ and $Z_2$ are each $(CH_2)_3CH_3$ as an orange crystalline solid (15.6 g., 48% yield based on the theoretical amount of compound of Formula VI, 27% yield for this step and the previous step combined).

The compound of Formula VI is prepared by condensing the corresponding compound having the structural formula

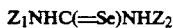   Formula VIII with diethyl malonate and sodium methoxide in ethanol under reflux. In an example diethyl malonate (128 g.) followed by the below-described 1,3-dibutylselenourea (the compound of Formula VIII wherein $Z_1$ and $Z_2$ are each $(CH_2)_3CH_3$, 90 g.) were added to a solution of sodium methoxide (49 g.) in absolute ethanol (160 ml.). More absolute ethanol (to a total volume of 750 ml.) was added and the mixture was refluxed with stirring under nitrogen. After 8 days more diethyl malonate (20 g.) was added and refluxing was continued for a total of 12 days. Water (1200 ml.) and sodium hydroxide (20 g.) were added. The mixture was refluxed for 2 hours, chilled, filtered to remove unreacted 1,3-dibutylselenourea (54 g.), decolorized and clarified with charcoal and diatomateous earth, and acidified with concentrated hydrochloric acid (about 150 ml.). Recrystallization of the resulting partly crystalline orange solid from hexane (about 700 ml.) gave the compound of Formula VI wherein $Z_1$ and $Z_2$ are each $(CH_2)_3CH_3$ (1,3-dibutyl-2-selenobarbituric acid) as a yellow crystalline solid (19.6 g., 42% yield corrected for recovered 1,3-dibutylselenourea).

The compound of Formula VIII is prepared by reaction of the corresponding compound having the structural formula

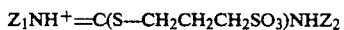   Formula IX with sodium hydrogen selenide in water at pH about 9 at a temperature in the range from 0° to 100° C. Sodium hydrogen selenide is prepared from elemental selenium and sodium borohydride in water containing a small amount of ethanol under nitrogen at room temperature. In an example sodium borohydride (9.0 g.) was added in small increments with stirring under nitrogen to a suspension of elemental selenium powder (15.8 g.) in water (350 ml.) containing a few ml. of ethanol until an essentially colorless solution resulted. Sodium carbonate (5 g.) was added to raise the pH to about 9.0.

The compound of Formula IX is prepared by reaction of the corresponding compound having the structural formula

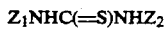   Formula X with 1,3-propanesultone without a solvent at a temperature in the range from 50° to 150° C. The compounds of Formula X are generally known and, if not specifically known, preparable by known methods. In an example a mixture of 1,3-dibutylthiourea (the compound of Formula X wherein $Z_1$ and $Z_2$ are each $(CH_2)_3CH_3$, 37.6 g.)

and 1,3-propanesultone (27 g.) was heated at about 120° C. until a high viscosity amber syrup was formed. Complete water solubility of a test sample was considered indicative that the reaction was complete. The melt was distributed in a thin layer on the wall of the reaction flask and chilled under running water to form an amber glass of the compound of Formula IX wherein $Z_1$ and $Z_2$ are each $(CH_2)_3CH_3$, which was dissolved with stirring in water (350 ml.). The resulting solution was added with stirring under nitrogen to the above-described preparation of sodium hydrogen selenide. A sample of the reaction mixture was removed and heated in a test tube until an oily precipitate occurred. The sample was chilled and seeded with a small amount of 1,3-dibutylthiourea to generate a crop of seed crystals which was added to the main reaction mixture, which was warmed to and kept at about 50° C. for about an hour, then permitted to cool to room temperature overnight. The resulting yellow crystalline solid was collected by filtration, washed with water and dried affording 1,3-dibutylselenourea (the compound of Formula VIII wherein $Z_1$ and $Z_2$ are each $(CH_2)_3C_3$, 40.0 g., 89.7% yield).

In the examples set forth below structures of products are inferred from structures of starting materials and expected courses of preparative reactions. Structural confirmation and estimation of purity of starting materials and products are measured by one or more of melting temperature range (m.r.), elemental analysis, infrared (IR) spectral analysis, ultraviolet (UV) and visible spectral analysis, nuclear magnetic resonance (NMR) spectral analysis, gas chromatography (GC), high pressure liquid chromatography (HPLC) and thin layer chromatography (TLC).

EXAMPLE 1

To a boiling solution of the compound of Formula II wherein X is S, m is 1, Ar is naphtho[2,3-d] and Y is $(CH_2)_3$ (prepared by condensing the corresponding compound of Formula IV with 1,3-propanesultone in the melt, 0.96 g.) and the above-described compound of Formula III wherein R' is methyl, p is 1 and $Z_1$ and $Z_2$ are each $(CH_2)_3CH_3$ (1.06 g.) in acetonitrile (150 ml.) was added a solution of triethylamine (0.5 g.) in acetonitrile (5 ml.). Boiling was continued for 5 minutes during which crystallization initiated spontaneously in the dark blue reaction mixture, which was then chilled overnight. The resulting blue-green solid (1.95 g., 90% yield) was collected by filtration and recrystallized from acetonitrile (500 ml.) affording as a dark green or black solid (1.50 g., 69% yield, visible absorption maximum at 613.5 nm. having an extinction coefficient of $2.48 \times 10^5$) the compound of Formula I wherein X is S, Y is $(CH_2)_3$, Z is $(CH_2)_3CH_3$, m is 1, n is 2, $M^+$ is triethylammonium ion and Ar is naphtho[2,3-d] having the structural formula:

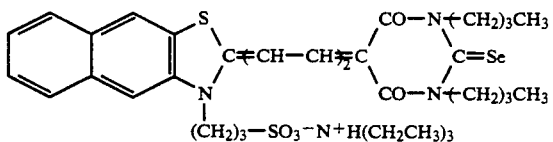

EXAMPLE 2

By the procedure of example 1 condensation of the compound of Formula II wherein X is S, m is 1, Ar is naphtho[1,2-d] and Y is $(CH_2)_3$ (prepared by condensing the corresponding compound of Formula IV with 1,3-propanesultone in the melt, 0.96 g.) with the above-described compound of Formula III wherein R' is methyl, p is 1 and $Z_1$ and $Z_2$ are each $(CH_2)_3CH_3$ (1.06 g.) in acetonitrile (200 ml.) with triethylamine (0.5 g.) as catalyst and purification of the resulting product by recrystallization from boiling acetonitrile (450 ml.) afforded as a dark blue crystalline solid (1.30 g., 60% yield, visible absorption maximum at 617.5 nm. having an extinction coefficient of $1.25 \times 10^5$) the compound of Formula I wherein X is S, Y is $(CH_2)_3$, Z is $(CH_2)_3CH_3$, m is 1, n is 2, $M^+$ is triethylammonium ion and Ar is naphtho[1,2-d] having the structural formula:

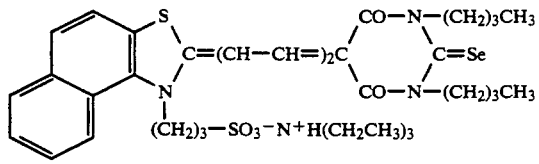

EXAMPLE 3

By the procedure of example 1 condensation of the compound of Formula II wherein X is S, m is 1, Ar is naphtho[2,1-d] and Y is $(CH_2)_3$ (prepared by condensing the corresponding compound of Formula IV with 1,3-propanesultone in the melt, 0.96 g.) with the above-described compound of Formula III wherein R' is methyl, p is 1 and $Z_1$ and $Z_2$ are each $(CH_2)_3CH_3$ (1.06 g.) in acetonitrile (150 ml.) with triethylamine (0.5 g.) as catalyst and purification of the resulting product by recrystallization from acetonitrile (300 ml.) afforded as a dark blue crystalline solid (0.90 g., 41% yield, visible absorption maximum at 617.0 nm. having an extinction coefficient of $1.43 \times 10^5$) the compound of Formula I wherein X is S, Y is $(CH_2)_3$, Z is $(CH_2)_3CH_3$, m is 1, n is 2, $M^+$ is triethylammonium ion and Ar is naphtho[2,1-d] having the structural formula:

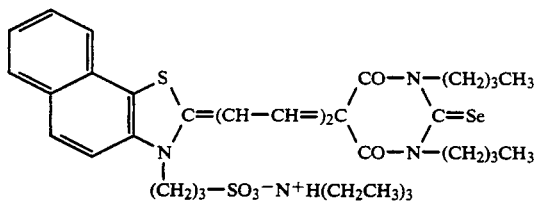

EXAMPLE 4

By the procedure of example 1 condensation of the compound of formula II wherein X is O, m is 1, Ar is benzo and Y is $(CH_2)_3$ (prepared by condensing the corresponding compound of Formula IV with 1,3-propanesultone in the melt, 0.77 g.) with the above-described compound of Formula III wherein R' is methyl, p is 1 and $Z_1$ and $Z_2$ are each $(CH_2)_3CH_3$ (1.06 g.) in acetonitrile (150 ml.) with triethylamine (0.5 g.) as catalyst, conversion of the resulting triethylammonium salt into the sodium salt by ion exchange using sodium iodide and purification of the resulting product by recrystallization from methanol afforded as a dark purple crystalline solid (1.13 g., 61% yield, visible absorption maximum at 567 nm. having an extinction coefficient of $1.50 \times 10^5$) the compound of Formula I wherein X is O, Y is $(CH_2)_3$, Z is $(CH_2)_3CH_3$, m is 1, n is 2, $M^+$ is sodium ion and Ar is benzo having the structural formula:

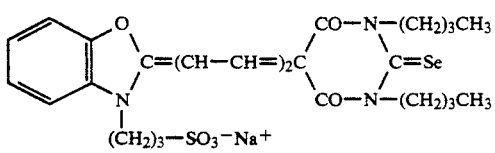

EXAMPLE 5

By the procedure of example 1 condensation of the compound of formula II wherein X is O, m is 1, Ar is benzo and Y is $(CH_2)_3$ (prepared by condensing the corresponding compound of Formula IV with 1,3-propanesultone in the melt, 0.84 g.) with the above-described compound of Formula III wherein R' is methyl, p is 1 and $Z_1$ and $Z_2$ are each $(CH_2)_3CH_3$ (1.06 g.) in acetonitrile (150 ml.) with triethylamine (0.5 g.) as catalyst, conversion of the resulting triethylammonium salt into the sodium salt by ion exchange using sodium iodide and purification of the resulting product by recrystallization from methanol afforded as a dark blue crystalline solid (1.30 g., 68% yield, visible absorption maximum at 602.0 nm. having an extinction coefficient of $1.53 \times 10^5$) the compound of Formula I wherein X is X, Y is $(CH_2)_3$, Z is $(CH_2)_3CH_3$, m is 1, n is 2, $M^+$ is sodium ion and Ar is benzo having the structural formula:

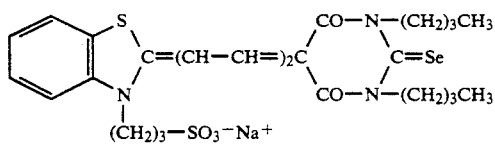

Physical Properties of the Compounds

The method of generating singlet oxygen using the compounds of Formula I can be carried out in any inert solvent. The preferred inert solvent is ethanol. The quantum yield for the process can be measured using a scavenger for singlet oxygen, for example diphenylisobenzofuran, photosensitized oxidation of which follows first order kinetics with a rate constant directly proportional to the quantum yield as described by Young et al. (Journal of the American Chemical Society, vol. 93, no. 22, pp. 5774–5779, 1971). By this method the quantum yields of the presently described compounds of Examples 3, 4 and 5 were measured and compared with the quantum yields of the corresponding prior art compounds of formulas F, A and D respectively. Relative quantum efficiencies were calculated from the results and are presented in Table I in each instance as the ratio of the quantum yield of the presently described compound to the quantum yield of the prior art compound.

TABLE I

| Relative Quantum Efficiencies | | |
|---|---|---|
| Presently Described Compound of | Prior Art Compound of | Ratio of Quantum Yield of Presently Described Compound to Quantum Yield of Prior Art Compound |
| Example 3 | Formula F | 74 |
| Example 4 | Formula A | 120 |

TABLE I-continued

| Relative Quantum Efficiencies | | |
|---|---|---|
| Presently Described Compound of | Prior Art Compound of | Ratio of Quantum Yield of Presently Described Compound to Quantum Yield of Prior Art Compound |
| Example 5 | Formula D | 60 |

These results are surprising in view of the fact that the quantum efficiency of the prior art compound of Formula B is only five times that of the prior art compound of Formula A, wherein selenium replaced oxygen in the azole ring. In the presently described compounds replacement of sulfur on the barbiturate ring with selenium results in about two orders of magnitude enhancement of relative quantum efficiencies.

Biological Properties of the Compounds

The method of inactivating a virus and inactivating cancer cells are carried out by contacting the virus or cancer cells with a solution of the compound of Formula I in a solvent which does not damage the tissue or normal cells in which the virus or cancer cells reside. Dilution into nutrient medium from a stock solution in aqueous ethanol is preferred. Visible light is preferably provided by cool white fluorescent tubes and has intensity from about 10 to about 100 watts per square meter.

Tests of the prior art compounds of Formulas A, B, D, E, F and G and Examples 1-5 were carried out against human herpes simplex virus type 1 grown in cultures of Vero cells 3 S in Hepes-buffered (10mM, pH 7.4) alpha-medium with fetal bovine serum (12% or 14%) using cool white fluorescent light delivering an illumination intensity of about 70 watts per square meter. A sufficient amount of a solution of each test compound in aqueous ethanol (50%) was added to the culture to make the concentration of test compound in the culture 3.3 micromolar. Reductions of viral titers measured in plaque forming units per milliliter (PFU/ml.) from initial values between $10^5$ and $10^8$ PFU/ml. were determined by serial dilution at intervals of 2, 4, 6, 8 and 10 minutes after the start of illumination and expressed as differences in log PFU/ml. values (log reduction values).

In a test of the prior art compounds of Formulas A, B, D, E, F and G at an initial virus titer of approximately $6.5 \times 10^5$ PFU/ml. the prior art compound of Formula F was found to be most potent and had log reduction values of 3.22, 3.52 and 4.12 at 2, 4 and 6 minutes after the start of illumination and log reduction values below the detectable limit at 8 and 10 minutes after the start of illumination. Accordingly the prior art compound of Formula F was used as the reference compound for further tests.

In a test of the prior art compound of Formula F and the presently described compounds of Examples 1-3 at an initial virus titer of approximately $1.06 \times 10^6$ PFU/ml. the results shown in Table II were obtained (* represents a log reduction value below the detectable limit).

TABLE II

| Test Against Herpes Simplex Virus | | | | | |
|---|---|---|---|---|---|
| | Log Reduction Value at Exposure Time (Minutes) | | | | |
| Compound of | 2 | 4 | 6 | 8 | 10 |
| Formula F | 3.40 | 4.05 | 4.46 | * | * |

TABLE II-continued

Test Against Herpes Simplex Virus

| Compound of | Log Reduction Value at Exposure Time (Minutes) | | | | |
|---|---|---|---|---|---|
| | 2 | 4 | 6 | 8 | 10 |
| Example 1 | * | * | * | * | * |
| Example 2 | 5.10 | 6.10 | * | * | * |
| Example 3 | * | * | * | * | * |

In a test of the prior art compound of Formula F and the presently described compounds of Examples 4 and 5 at an initial virus titer of approximately $1.5 \times 10^7$ PFU/ml the results shown in Table III were obtained (* represents a log reduction value below the detectable limit).

TABLE III

Test Against Herpes Simplex Virus

| Compound of | Log Reduction Value at Exposure Time (Minutes) | | | | |
|---|---|---|---|---|---|
| | 2 | 4 | 6 | 8 | 10 |
| Formula F | 3.35 | 4.12 | 4.82 | 5.37 | 6.22 |
| Example 4 | 4.37 | 4.72 | 5.52 | * | * |
| Example 5 | 4.43 | 4.49 | 4.74 | 4.74 | 4.82 |

In a test of the prior art compound of Formula F and the presently described compounds of Examples 1-5 at an initial virus titer of approximately $3.95 \times 10^7$ PFU/ml. and an approximately 0.65 micromolar concentration instead of an approximately 3.3 micromolar concentration of test compound the results shown in Table IV were obtained.

TABLE IV

Test Against Herpes Simplex Virus

| Compound of | Log Reduction Value at Exposure Time (Minutes) | | | | |
|---|---|---|---|---|---|
| | 2 | 4 | 6 | 8 | 10 |
| Formula F | 1.12 | 1.89 | 2.49 | 3.05 | 3.47 |
| Example 1 | 4.10 | 4.30 | 4.35 | 4.40 | 4.46 |
| Example 2 | 1.40 | 1.82 | 2.46 | 2.82 | 2.92 |
| Example 3 | 3.64 | 3.70 | 3.70 | 4.35 | 4.46 |
| Example 4 | 1.18 | 1.92 | 3.02 | 3.07 | 3.12 |
| Example 5 | 1.74 | 1.92 | 2.02 | 2.07 | 2.12 |

In a test of the prior art compound of Formula F and the presently described compounds of Examples 1 and 3 at an initial virus titer of approximately $3.95 \times 10^7$ PFU/ml., an approximately 0.88 micromolar concentration instead of an approximately 3.3 micromolar concentration of test compound and a light intensity of 35 watts per square meter instead of 70 watts per square meter the results shown in Table V were obtained.

TABLE V

Test Against Herpes Simplex Virus

| Compound of | Log Reduction Value at Exposure Time (Minutes) | | | | |
|---|---|---|---|---|---|
| | 2 | 4 | 6 | 8 | 10 |
| Formula F | 0.70 | 1.00 | 1.10 | 1.52 | 1.74 |
| Example 1 | 2.00 | 2.82 | 3.40 | 4.52 | 5.60 |
| Example 3 | 1.74 | 2.89 | 3.57 | 4.26 | 4.30 |

In a test of the prior art compound of Formula F and the presently described compounds of Examples 1 and 3 at an initial virus titer of approximately $3.95 \times 10^7$ PFU/ml., an approximately 0.88 micromolar concentration instead of an approximately 3. micromolar concentration of test compound, a light intensity of 35 watts per square meter instead of 70 watts per square meter and exposure of the viral culture to the test compound for 30 minutes before illumination the results shown in Table VI were obtained (* represents a log reduction value below the detectable limit).

TABLE VI

Test Against Herpes Simplex Virus

| Compound of | Log Reduction Value at Exposure Time (Minutes) | | | | |
|---|---|---|---|---|---|
| | 2 | 4 | 6 | 8 | 10 |
| Formula F | 0.98 | 1.10 | 1.52 | 1.52 | 2.05 |
| Example 1 | 2.10 | 3.05 | 4.60 | 6.30 | * |
| Example 3 | 1.70 | 2.00 | 2.70 | 3.00 | 3.30 |

The results set forth in Tables II-VI show that, except the presently described compound of Example 5 at longer exposure times, the presently described compounds of Examples 1-5 are at least as potent and up to three orders of magnitude more potent than the prior art compound of Formula F in the tests against herpes simplex virus.

Tests of the prior art compounds of Formulas A and F and the presently described compounds of Examples 1-5 were carried out against cultures of human K562 leukemia cells and human A549 lung carcinoma cells in Hepes-buffered (10mM, pH 7.4) alpha-medium with fetal bovine serum (14%) using cool white fluorescent light having an intensity of about 70 watts per square meter. A sufficient amount of a solution of each test compound in aqueous ethanol (50%) was added to the culture to make the concentration of test compound in the culture 13.15 micromolar. Reductions of cell titers measured in colony forming units per milliliter (CFU/ml.) were determined by serial dilution at intervals of 10, 20 and 30 minutes (leukemia cells) or 15, 30, 45, 60, 75 and 90 minutes (lung carcinoma cells) after addition of the test compound and expressed as differences in log CFU/ml. values (log reduction values).

In a test of the prior art compound of Formula A and the presently described compounds of Examples 1-3 against human K562 leukemia cells the results shown in Table VII were obtained.

TABLE VII

Test Against Leukemia Cells

| Compound of | Log Reduction Value at Exposure Time (Minutes) | | |
|---|---|---|---|
| | 10 | 20 | 30 |
| Formula A | 0.05 | 0.15 | 0.30 |
| Example 1 | 2.22 | 2.52 | 4.40 |
| Example 2 | 0.22 | 0.46 | 1.52 |
| Example 3 | 2.52 | 2.74 | 3.82 |

In a test of the prior art compound of Formula F and the presently described compounds of Examples 4 and 5 against human K562 leukemia cells the results shown in Table VIII were obtained.

TABLE VIII

Test Against Leukemia Cells

| Compound of | Log Reduction Value at Exposure Time (Minutes) | | |
|---|---|---|---|
| | 10 | 20 | 30 |
| Formula F | 0.43 | 1.40 | 2.66 |
| Example 4 | 1.46 | 2.07 | 2.30 |
| Example 5 | 0.66 | 0.92 | 1.22 |

In a test of the prior art compound of Formula F and the presently described compounds of Examples 1-3 against human A549 lung carcinoma cells the results shown in Table IX were obtained.

TABLE IX

| Compound of | Test Against Lung Carcinoma Cells Log Reduction Value at Exposure Time (Minutes) | | | | | |
|---|---|---|---|---|---|---|
| | 15 | 30 | 45 | 60 | 75 | 90 |
| Formula F | 0.30 | 0.35 | 0.66 | 0.85 | 0.92 | 1.46 |
| Example 1 | 0.52 | 2.35 | 2.41 | 2.57 | 2.74 | 2.92 |
| Example 2 | 0.00 | 0.00 | 0.00 | 0.00 | 0.12 | 0.22 |
| Example 3 | 2.00 | 2.57 | 2.57 | 2.70 | 2.74 | 2.82 |

In a test of the prior art compound of Formula F and the presently described compounds of Examples 4 and 5 against human A549 lung carcinoma cells the results shown in Table X were obtained.

TABLE X

| Compound of | Test Against Lung Carcinoma Cells Log Reduction Value at Exposure Time (Minutes) | | | | | |
|---|---|---|---|---|---|---|
| | 15 | 30 | 45 | 60 | 75 | 90 |
| Formula F | 0.05 | 0.49 | 0.60 | 0.77 | 0.82 | 0.92 |
| Example 4 | 1.03 | 1.26 | 1.38 | 1.74 | 1.72 | 1.82 |
| Example 5 | 0.12 | 0.26 | 0.38 | 0.40 | 0.40 | 0.77 |

The results set forth in Tables VII–X show that, except the presently described compounds of Examples 2 and 5 against leukemia cells and the presently described compound of Example 2 against lung carcinoma cells, the presently described compounds of Examples 1-5 are at least as potent and up to four orders of magnitude more potent than the prior art compound of Formula A or the prior art compound of Formula F in the tests against leukemia cells and lung carcinoma cells.

Photographic Compositions

The silver halide photographic emulsions of the invention are prepared with conventional ingredients by conventional methods. The photosensitizingly effective amount of the compound of Formula I is preferably in the range from 0.1 micromolar to 100 micromolar.

We claim:

1. A compound having the structural formula

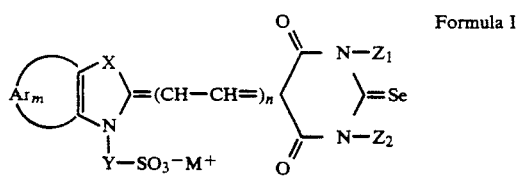

Formula I wherein
X is O, S, Se, Te, C(CH$_3$)$_2$ or NR wherein R is methyl, ethyl, propyl, cyclopropyl, cyclohexyl, phenyl or phenyl substituted by from one to three of methyl, trifluoromethyl, methoxycarbonyl, ethoxycarbonyl, cyano, dimethylamino, methoxy, methylthio, fluoro, chloro, bromo, or iodo;
Y is alkylene having from two to nine carbon atoms or alkylene having from two to nine carbon atoms interrupted by O, S, NR', CONH or phenylene wherein R' is methyl or phenyl;
Z$_1$ and Z$_2$ are independently H or alkyl having from one to ten carbon atoms;
m is 0 or 1;
n is 1, 2 or 3;
M$^+$ is pharmaceutically or photographically acceptable cation; and
Ar is a fused aromatic nucleus selected from the group consisting of benzo and naphtho.

2. A compound according to claim 1 wherein X is O or S, Y is (CH$_2$)$_3$, Z$_1$ and Z$_2$ are each (CH$_2$)$_3$CH$_3$, m is 1, n is 2.

3. A compound according to claim 2 wherein Ar is benzo.

4. A compound according to claim 3 wherein X is O.

5. The compound according to claim 4 having the structural formula:

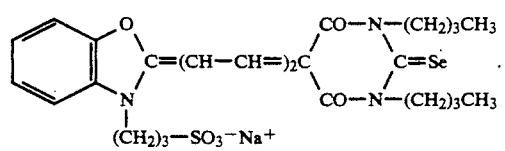

6. A compound according to claim 3 wherein X is S.

7. The compound according to claim 6 having the structural formula:

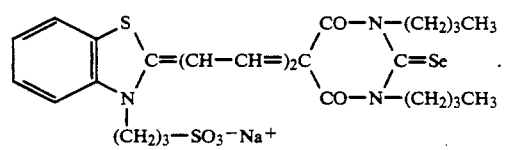

8. A compound according to claim 2 wherein X is S and Ar is naphtho[1,2-d].

9. The compound according to claim 8 having the structural formula:

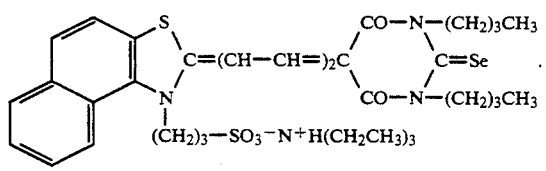

10. A compound according to claim 2 wherein X is S and Ar is naphtho[1,2-d].

11. The compound according to claim 10 having the structural formula:

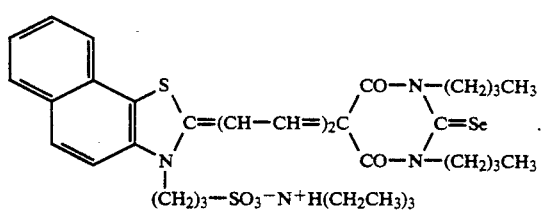

12. A compound according to claim 2 wherein X is S and Ar is naphtho[2,3-d].

13. The compound according to claim 12 having the structural formula:

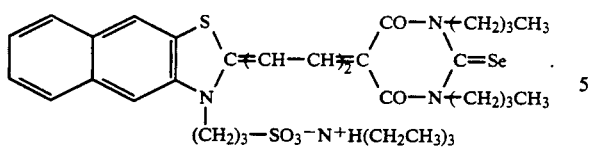
(CH₂)₃—SO₃⁻N⁺H(CH₂CH₃)₃

14. The process for preparing a compound of Formula I according claim 1 comprising condensing the corresponding compound having the structural formula

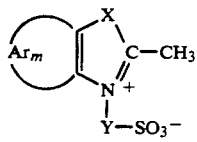

Formula II with the corresponding compound having the structural formula

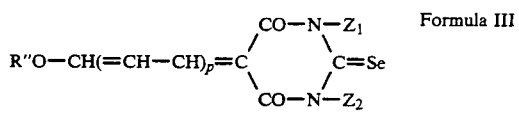

Formula III wherein R″ is methyl or ethyl and p is 0, 1 or 2 using a basic tertiary amine catalyst in an inert solvent at a temperature in the range from 0° C. to 100° C.

15. The process according to claim 14 wherein X is O or S, $Z_1$ and $Z_2$ are each $(CH_2)_3CH_3$, m is 1, n is 2, Ar is benzo or naphtho, R″ is methyl and p is 1.

16. The process according to claim 15 wherein X is O or S and Ar is benzo.

17. The process according to claim 15 wherein X is S and Ar is naphtho[1,2-d], naphtho[2,1-d] or naphtho[2,3-d].

* * * * *